United States Patent [19]

Everly

[11] 4,405,528

[45] Sep. 20, 1983

[54] METHOD OF PREPARING 4-(α-ALKYL-α-CYANO-METHYL)2,6-DI-SUBSTITUTED PHENOLS

[75] Inventor: Charles Everly, Baton Rouge, La.

[73] Assignee: Ethyl Corporation, Richmond, Va.

[21] Appl. No.: 385,610

[22] Filed: Jun. 7, 1982

[51] Int. Cl.³ .................... C07C 121/75; C07C 59/11
[52] U.S. Cl. .................................. 260/465 F; 562/478
[58] Field of Search ................... 260/465 F; 562/478

[56] References Cited

U.S. PATENT DOCUMENTS 4,178,460  12/1979  Berkelhammer et al. .......... 562/426
4,199,595   4/1980  Berkelhammer et al. .......... 424/304

OTHER PUBLICATIONS

Volod'kin et al., *Iz. Akad. Nauk. SSSR, Ser. Khim*, 1030–1032, (1966).
Kudinova et al., *Iz. Akad. Nauk. SSSR, Ser. Khim*, 1313–1317, (1978).
Schwartz et al., *J. Org. Chem.*, vol. 41, 2502 (1976).
Hay, *J. Org. Chem.*, vol. 34, 1160 (1969).
*Advanced Organic Chemistry*, (McGraw-Hill, New York, 1977), pp. 809–810.

Primary Examiner—Dolph H. Torrence
Attorney, Agent, or Firm—Donald L. Johnson; John F. Sieberth; Willard G. Montgomery

[57] ABSTRACT

4-(α-alkyl-α-cyano-methyl)2,6-di-substituted phenols having the formula

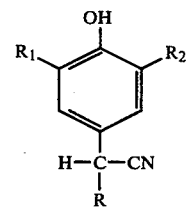

wherein R is methyl, ethyl, n-propyl or isopropyl are prepared by reacting a di-substituted phenol, such as 2,6-di-tertiary-butyl phenol, with a Friedel-Crafts addition agent in the presence of a Friedel-Crafts catalyst such as aluminum chloride to form the corresponding 4-(α-alkyl-α-oxo-methyl)2,6-di-substituted phenol. The 4-(α-alkyl -α-oxo-methyl)2,6-di-substituted phenol thus formed readily can be reduced to form the corresponding 4-(α-alkyl-α-hydroxy-methyl)2,6-di-substituted phenol which thereafter can be reacted with an alkali metal or an alkaline earth metal cyanide to form the desired 4-(α-alkyl-α-cyano-methyl)2,6-di-substituted phenol. This can be converted by hydrolysis into the corresponding α-alkyl-4-hydroxyphenylacetic acid. These acids are well-known insecticidal and acaricidal intermediates.

31 Claims, No Drawings

METHOD OF PREPARING 4-(α-ALKYL-α-CYANO-METHYL)2,6-DI-SUBSTITUTED PHENOLS

TECHNICAL FIELD

This invention relates to a novel process for the preparation of 4-(α-alkyl-α-cyano-methyl)2,6-di-substituted phenol. Further, this invention relates to 4-(α-alkyl-α-cyano-methyl)2,6-di-substituted phenols which are produced in a novel synthesis reaction and are used as intermediates in a reaction sequence in which α-alkyl-4-hydroxyphenylacetic acids are produced which in turn are used as reaction intermediates in the preparation of insecticides of m-phenoxybenzyl and α-cyano-m-phenoxybenzyl esters.

BACKGROUND

Meta-phenoxybenzyl esters and α-cyano-m-phenoxybenzyl esters of 2-haloalkyl(oxy-, thio-, sulfinyl-, or sulfonyl)phenylalkanoic acids are known insecticidal and acaricidal agents. These compounds and methods for their preparation are disclosed in Berkelhammer et. al., U.S. Pat. Nos. 4,178,460 and 4,199,595. In both Berkelhammer et al. U.S. Pat. Nos. 4,178,460 and 4,199,595, there is disclosed the conversion of certain α-alkyl-3(or 4)-hydroxyphenylacetic acids having the formula

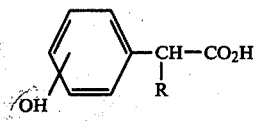

wherein R is ethyl, n-propyl or isopropyl to the corresponding α-alkyl-3(or 4)-difluoromethoxyphenylacetic acids having the formula

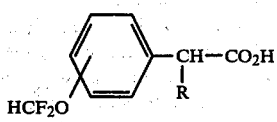

wherein R is as defined above by treatment with chlorodifluoromethane in aqueous alkali and dioxane. The α-alkyl-3(or 4)-difluoromethoxyphenylacetic acids thus formed are then treated with thionyl chloride, thionyl bromide, or the like, preferably in the presence of an aromatic solvent such as benzene or toluene, to yield α-alkyl(substituted phenyl)acetyl halide which is reacted with m-phenoxybenzyl alcohol or α-cyano-m-phenoxybenzyl alcohol to yield the desired m-phenoxybenzyl ester or α-cyano-m-phenoxybenzyl ester of the 2-haloalkyl(oxy-, thio-, sulfinyl- or sulfonyl)phenylalkanoic acids which are useful insecticides. In Berkelhammer et. al., U.S. Pat. Nos. 4,178,460 and 4,199,595, the α-alkyl-3(or 4)-hydroxyphenylacetic acid intermediate is prepared by reacting the appropriate α-alkyl-3(or 4)-methoxyphenylacetonitrile with hydrobromic acid.

A new process for the synthesis of α-alkyl-4-hydroxyphenylacetic acids now has been discovered in which these materials can be prepared in a simple and straightforward manner. In this new process, 4-(α-alkyl-α-cyano-methyl)-2,6-di-substituted phenol as intermediates in a reaction sequence in which α-alkyl-4-hydroxyphenylacetic acids are likewise produced and used as reaction intermediates.

Methods are known for preparing 4-(α-alkyl-α-cyano-methyl)2,6-di-substituted phenols. For example, the preparation of 4-(α-alkyl-α-cyano-methyl)2,6-di-substituted phenol by reacting α-alkyl-4-hydroxy-3,5-di-tertiary-butylbenzyl halides with sodium cyanide is reported by A. A. Volod'kin et. al., *Iz. Akad. Nauk. SSSR, Ser. Khim,* 1966, 1031. Also, the preparation of 4-(α-alkyl- -cyano-methyl)2,6-di-substituted phenols by the electrochemical reduction of the corresponding 2,6-di-substituted methylenequinone is reported by L. I. Kudinova, et. al., *Iz. Akad. Nauk. SSSR, Ser. Khim.,* 1978, 1313. In U.S. application Ser. No. 385,609, entitled "Preparation of 4-(α-Alkyl-α-Cyano-Methyl)2,6-Di-Substituted Phenol" filed on June 7, 1982, there is disclosed a novel process for the synthesis of 4-(α-alkyl-α-cyano-methyl)2,6-di-substituted phenol by reacting a 2,6-di-substituted phenol with an aliphatic aldehyde selected from formaldehyde, acetaldehyde, propionaldehyde or butyraldehyde and an alkali metal cyanide or an alkaline earth metal cyanide in a suitable reaction solvent to form the corresponding 4-(α-alkyl-α-cyano-methyl)2,6-di-substituted phenol.

The synthesis of o- and p-hydroxy substituted phenylacetonitriles also is known and is reported in the literature. See, for example, *Journal of Organic Chemistry,* Vol. 41, No. 14, 2502 (1976).

THE INVENTION

This invention thus involves in a preferred embodiment the discovery that 4-(α-alkyl-α-cyano-methyl)2,6-di-substituted phenol readily can be prepared in good yield with high selectivity by reacting a 2,6-di-substituted phenol with a Friedel-Crafts addition agent in the presence of a Friedel-Crafts catalyst to form the corresponding 4-(α-alkyl-α-oxo-methyl)2,6-di-substituted phenol, reducing the 4-(α-alkyl-α-oxo-methyl)2,6-di-substituted phenol thus produced to form the corresponding 4-(α-alkyl-α-hydroxy-methyl)2,6-di-substituted phenol and thereafter, reacting the 4-(α-alkyl-α-hydroxy-methyl)2,6-di-substituted phenol with an alkali metal or an alkaline earth metal cyanide in a suitable solvent to form the desired 4-(α-alkyl-α-cyano-methyl)2,6-di-substituted phenol.

In another embodiment of this invention, α-alkyl-4-hydroxyphenylacetic acid is produced by (1) forming a 4-(α-alkyl-α-cyano-methyl)2,6-di-substituted phenol in the above manner, (2) dealkylating the substituent groups ortho to the hydroxyl group from the 4-(α-alkyl-α-cyano-methyl)2,6-di-substituted phenol to produce a reaction product containing a substantial amount of the corresponding 4-(α-alkyl-α-cyano-methyl)phenol, and (3) thereafter converting the 4-(α-alkyl-α-cyano-methyl)phenol to the corresponding α-alkyl-4-hydroxyphenylacetic acid by hydrolysis.

The phenols which may be used as starting materials in the process of the invention are phenols having the general formula

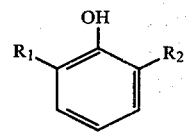

wherein each R is the same or different monovalent substituent selected from the group consisting of alkyl, aralkyl and cyclic alkyl radicals. These phenols are reacted in a liquid phase with a Friedel-Crafts addition agent in the presence of a Friedel-Crafts catalyst to form the corresponding 4-(α-alkyl-α-oxo-methyl)2,6-di-substituted phenol which is subsequently reduced to form the corresponding 4-(α-alkyl-α-hydroxy-methyl)2,6-di-substituted phenol which in turn is hydrolyzed to the corresponding 4-(α-alkyl-α-cyano-methyl)2,6-di-substituted phenol.

Typical examples of alkyl, aralkyl and cyclic alkyl radicals which $R_1$ and $R_2$ may be include any of the above radicals having any number of carbon atoms as long as these substituents do not interfere either with the formation of the desired 4-(α-alkyl-α-cyano-methyl)2,6-di-substituted phenol or with the subsequent dealkylation of the 4-(α-alkyl-α-cyano-methyl)2,6-di-substituted phenol to produce the corresponding 4-(α-alkyl-α-cyano-methyl)phenol from which the corresponding α-alkyl-4-hydroxyphenylacetic acid is made. These may include, for example, from 1 to 40 carbon atoms and the alkyl radicals may include primary, secondary or tertiary alkyl groups and cycloalkyl groups. Since the most readily available of the substituted phenols are those phenols having substituents of from 1 to about 8 carbon atoms they are preferred, but the invention is not limited thereto. Examples of typical substituents include methyl, ethyl, propyl, isopropyl, the isomeric butyl radicals (i.e., n-butyl, isobutyl, cyclobutyl, t-butyl, etc.), the isomeric amyl radicals, the isomeric hexyl radicals, the isomeric decyl radicals, the isomeric hexadecyl radicals, the isomeric eicosyl radicals, the isomeric tricosyl radicals, the isomeric triacontyl radicals, etc. The alkyl radicals may be substituted with aryl, preferably monocyclic aryl radicals, or cycloalkyl radicals, for example, benzyl, phenylethyl, cyclohexylethyl, naphthylethyl, etc. Examples of aryl radicals are phenyl, tolyl, xylyl, biphenylyl, naphthyl, methylnaphthyl, ethylphenyl, cyclohexophenyl, etc. Because the phenols in which the R substituents are methyl, ethyl, propyl, butyl, sec-butyl, isopropyl, t-butyl, amyl, sec-amyl, t-amyl, hexyl, heptyl, octyl, etc., or phenyl are either readily available commercially or easily made and are ideally suited for the process, the most preferred substituents are where $R_1$ and $R_2$ are a lower alkyl group (i.e., from 1 to about 8 carbon atoms) or phenyl.

Examples of phenols having the R substituents groups noted above which are preferred starting materials include 2,6-di-methylphenol; 2,6-di-sec-butylphenol, 2,6-diisopropylphenol, 2,6-di-sec-octylphenol, 2,6-di(α-methylbenzyl)phenol, 2-amyl-6-methylphenol, 2,6-dibenzylphenol, 2-methyl-6-benzylphenol and the like. A particularly useful phenol reactant for use in the practice of the process is 2,6-di-tert-butylphenol.

Substituent R groups other than those previously listed such as aryl, chlorine, bromine, fluorine, nitro groups, and the like may be present at the 2- and 6-positions in the aromatic phenol compound providing they do not adversely effect the formation of the 4-(α-alkyl-α-cyano-methyl)2,6-di-substituted phenol or the subsequent dealkylation of the condensation reaction product to the corresponding 4-(α-alkyl-α-cyano-methyl)phenol.

As used herein, the term Friedel-Crafts addition agent refers to acyl halides having the formula

wherein R is methyl, ethyl, n-propyl or isopropyl and X is —Cl, —Br, or —I. Further, the term Friedel-Crafts type catalyst refers to electron acceptors or Lewis acids which are used in conducting substitution reactions on a benzene type nucleus. These include metal salts, metal halides, acids, acid anhydrides and halides of certain metalloids. These catalysts which are liquids, solids, or gases are conveniently employed. Examples of these are $AlCl_3$, $AlBr_3$, $FeCl_3$, $PCl_3$, $PCl_5$, $BF_3$, $ZnCl_2$, $TiCl_4$, HF, $H_2SO_4$, $H_3PO_4$, $P_2O_5$, $TeCl_2$ and $SnCl_4$. Aluminum halides, and particularly anhydrous aluminum chloride, are preferred in the practice of this invention as these are readily available and give good yields of product.

The reaction between the addition agent and sterically hindered phenols not having a substituent in the para-position, such as 2,6-di-tert-butylphenol, under the condition of the Friedel-Crafts reaction to form the corresponding aliphatic-aromatic ketones of the sterically hindered phenols is known and reported in the literature. See, for example, N.V. Portnykh et. al., Iz. Akad. Nauk. SSSR. Ser. Khim., 1966, 2181–2182, and references cited therein, all disclosures of which are incorporated herein by reference. Portnykh et. al., report that for best results the reaction should be run in the medium of the acyl halide without a solvent at atmospheric pressure at −10° C. for 1 to 10 minutes in the presence of a Friedel-Crafts catalyst such as aluminum chloride. Recovery of the desired 4-(α-alkyl-α-oxo-methyl)2,6-di-substituted phenol product is achieved by conventional techniques such as distillation, crystallization or extraction techniques.

Various known procedures may be used for reducing the ketone substituent of the 4-(α-alkyl-α-oxy-methyl)2,6-di-substituted phenol to an alcohol substituent. By way of example, the reduction may be effected using iron powder and dilute acetic or hydrochloric acid, or by hydrogenation using a suitable catalyst such as platinum, palladium, nickel, or the like. Reduction using metal hydrides such as lithium aluminum hydride, lithium borohydride and sodium borohydride (carried out either in water or in aqueous alcohol such as methanol and ethanol, acetonitrile, etc.) is preferred. The conditions used for effecting such reductions are well known and reported in the literature. See, for example, March, *Advanced Organic Chemistry* (McGraw-Hill, New York, 1977), pp. 810–834 and Becker et. al., Organicum (Pergamon Press LTD-Oxford, 1973), pp. 521–524, and references cited therein, all disclosures of which are incorporated herein by reference.

Conversion of the 4-(α-alkyl-α-hydroxy-methyl)2,6-di-substituted phenol to the corresponding 4-(α-alkyl-α-cyano-methyl)2,6-di-substituted phenol is achieved by reacting the 4-(α-alkyl-α-hydroxy-methyl)2,6-di-substituted phenol with an alkali metal cyanide or an alkaline earth metal cyanide in the presence of a suitable solvent at elevated temperature.

The alkali and alkaline earth metal cyanide reactants which can be used in the present process may include sodium cyanide, potassium cyanide, lithium cyanide, magnesium cyanide and calcium cyanide. Ammonium cyanide also may be used in the practice of the process as well as hydrogen cyanide. Sodium cyanide is a preferred cyanide reactant.

The reaction is carried out in the liquid phase which is provided by using a solvent which is inert under the reaction conditions. That is, the reaction is carried out in the presence of a solvent which does not enter into the reaction. Preferred solvents are aprotic solvents which include ethers such as diethyl ether, dibutyl ether, 1-ethoxyhexane, tetrahydrofuran, 1,4-dioxane, 1,3-dioxolane, diglyme, 1,2-diethoxyethane and tertiary amines such as pyridine, N-ethylpiperidine, triethylamine, tributylamine, N,N-diphenyl-N-methyl amine, N,N-dimethylalanine, etc. Especially preferred solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc. Additionally, lower alkanols having up to about 6 carbon atoms also may be used. These include methanol, ethanol, n-propanol, isopropyl alcohol, n-butanol, sec-butyl alcohol, tert-butyl alcohol, n-pentanol, isopentyl alcohol, n-hexanol and isohexyl alcohol. In addition, a small amount of water can be added to the reaction mixture to facilitate the solubilization of the cyanide-containing reactant in the mixture.

The reaction is readily conducted by placing the phenol intermediate and the other reaction mixture components in a reaction vessel having agitation means. The process is preferably conducted in a substantially anhydrous reaction system and, accordingly, the components of the reaction system should be brought together and maintained under a substantially dry, inert atmosphere. Thus, while it is possible to conduct this process in the presence of air or moisture, as when water is added to the reaction mixture, it is desirable to maintain the reaction system under an atmosphere of dry nitrogen or the like.

The mode of addition is not particularly critical. Accordingly, it is convenient to add the phenol reactant to a mixture of the other materials, add the cyanide reactant to a mixture of the other materials, introduce all ingredients simultaneously into the reaction zone or the like. The process should be carried out for a time sufficient to convert substantially all of the phenol reactant to the corresponding 4-($\alpha$-alkyl-$\alpha$-cyano-methyl)2,6-di-substituted phenol intermediate. In general, the length of time for optimum yield depends primarily on the reaction temperature and the particular solvent used in the reaction. However, reaction ordinarily proceeds very rapidly and thus, long reaction times are not required. The reaction can be completed in the matter of minutes or at most a few hours at the reaction conditions.

Although the reaction will proceed at a very slow rate at ambient temperatures, it is covenient to conduct the reaction at an elevated temperature of at least about 50° C. up to the decomposition temperature of any of the reactants or the products. Ambient atmospheric pressure can be used or pressures lower or higher than ambient pressure can be used. However, there is no advantage to using less than ambient pressure. Higher than ambient pressure conditions are usually used if temperatures higher than the boiling point at atmospheric conditions of the reaction mixture are being used. However, by proper choice of the solvent to form the liquid phase desired, temperatures can be reached within the range of about 50° C. up to the reflux temperature of the reaction mixture at ambient atmospheric conditions which give a suitable reaction rate.

Conversion of the di-substituted phenol reactant to the corresponding 4-($\alpha$-alkyl-$\alpha$-cyano-methyl)2,6-di-substituted phenol in accordance with the practice of the invention results in substantially very little by-product formation, primarily unreacted phenol. Recovery of the product is achieved by conventional means such as evaporation and water wash or extraction with a suitable organic solvent.

For best results, it is desirable to employ an excess of the cyanide reactant relative to the phenol reactant. Normally, the reaction system will contain at least one molar equivalent of cyanide per mole of phenol reactant and preferably the molar ratio of the cyanide to the phenol is 2 or more.

Conversion of the 4-($\alpha$-alkyl-$\alpha$-cyano-methyl)2,6-di-substituted phenol to the corresponding $\alpha$-alkyl-4-hydroxyphenylacetic acid is carried out by dealkylating the substituent groups ortho to the hydroxyl group from the 4-($\alpha$-alkyl-$\alpha$-cyano-methyl)2,6-di-substituted phenol to form the corresponding 4-($\alpha$-alkyl-$\alpha$-cyano-methyl)phenol and then converting by hydrolysis the 4-($\alpha$-alkyl-$\alpha$-cyano-methyl)phenol to the corresponding $\alpha$-alkyl-4-hydroxyphenylacetic acid as disclosed in aforementioned U.S. application Ser. No. 385,609, entitled "Preparation of 4-($\alpha$-Alkyl-$\alpha$-Cyano-Methyl)2,6-Di-Substituted Phenol", filed on June 7, 1982 incorporated herein by reference as if fully set forth.

As set forth therein, any of the various dealkylation procedures using conditions and catalysts known in the art for causing dealkylation may be used in removing the substituent groups ortho to the hydroxyl group from the 4-($\alpha$-alkyl-$\alpha$-cyano-methyl)2,6-di-substituted phenol to produce a reaction product containing a substantial amount of the corresponding 4-($\alpha$-alkyl-$\alpha$-cyano-methyl)phenol intermediate providing they do not interfere with the course of the reaction. Preferably, dealkylation is achieved in high yield at elevated temperatures using an aluminum phenoxide or a Lewis acid catalyst in the presence of an aromatic or substituted aromatic compound. The conditions used for such dealkylations are well known and are reported in the literature. See, for example, *Journal of Organic Chemistry*, Vol. 34, 1160 (1969) and references cited therein, all disclosures of which are incorporated herein by reference.

The dealkylation process most conveniently employed comprises heating the 2,6-di-substituted phenol at an elevated temperature below the decomposition temperature of the desired 4-($\alpha$-alkyl-$\alpha$-cyano-methyl)-phenol intermediate product, such as from about 60° C. to 250° C. in the presence of a dealkylation catalyst and an aromatic hydrocarbon or a substituted aromatic hydrocarbon, such as, for example, benzene, toluene, xylene and the like. Although it is not a requirement of the dealkylation process, the reaction can be carried out under an inert, non-reactive atmosphere, such as nitrogen, if desired.

In the reaction, the aromatic compound serves both as a solvent for the reaction and as an acceptor for the substituent groups ortho to the hydroxyl group in the 4-($\alpha$-alkyl-$\alpha$-cyano-methyl)2,6-di-substituted phenol reactant which are dealkylated in a transalkylation process. Dealkylation results in the formation of substituted aromatic by-products such as, for example, a mixture of ortho- and para-tertiary-butyltoluene when toluene is employed as the aromatic compound in the reaction from which the desired 4-(α-alkyl-α-cyano-methyl)-phenol intermediate product can be separated and recovered using well-known techniques such as distillation, fractional distillation, crystallization or extraction techniques, etc. It is not necessary, however, to first recover the desired intermediate phenol product from the reaction mixture prior to subsequent hydrolysis of the intermediate to the corresponding acid.

For best results, it is desirable to employ an excess of aromatic or substituted aromatic compound relative to the di-substituted phenol reactant. Normally, the reaction system will contain at least 2 molar equivalents of aromatic reactant per mole of alkylated phenol reactant and preferably the molar ratio of the aromatic reactant to the alkylated phenol reactant is more than 2.

Aromatic hydrocarbons or substituted aromatic hydrocarbons which may be used in the dealkylation reaction include benzene, toluene, ethylbenzene, xylene, trimethylbenzene, tetrahydronaphthylene, isobutylbenzene, phenols (e.g., phenol, cresol, o-isopropylphenol, 4-hydroxyanisole (mono-, di-, and tribromophenol, etc.), halobenzenes (e.g., mono-, di-, and trifluorobenzenes, chlorobenzenes, bromobenzenes, chlorobromobenzenes), aromatic ethers (e.g., anisole, diphenylether, etc.), and the like.

Dealkylation of the substituted phenol in accordance with the invention is conducted, for example, by charging to a suitable reaction vessel the substituted phenol of choice, solvent and dealkylation catalyst, optionally under a blanket of nitrogen, and then heating to a temperature below the decomposition temperature of the desired 4-(α-alkyl-α-cyano-methyl)phenol intermediate product, but high enough to effect dealkylation of the substituted phenol.

As pointed out hereinabove, the dealkylation reaction can be conducted over a wide temperature range below the decomposition temperature of the desired dealkylated product. While the reaction will proceed at ambient temperatures at a very slow rate, in general, dealkylation is carried out at a temperature range of from about 60° C. to about 250° C. and will vary within this range depending upon the solvent of choice.

In general, dealkylation is carried out at atmospheric pressure although pressures above atmospheric pressure can be used if desired.

The dealkylation reaction should be carried out for a time sufficient to convert substantially all of the substituted phenol starting material to the desired dealkylated phenol intermediate product. The length of time required to obtain substantially complete dealkylation of the substituted phenol will depend primarily upon the operating temperature and the particular substituted phenol used in the reaction.

A wide variety of catalysts known in the art for causing dealkylation may be used in the practice of the process. For example, dealkylation catalysts such as phenoxy derivatives of such elements as aluminum, magnesium, iron, zinc, phosphorus, zirconium, titanium, bismuth, tin, etc., where the phenoxy moiety may be the phenoxy radical itself, the cresoxy radical, the xyloxy radical, etc. Also, Lewis acids, preferably aluminum chloride, zinc chloride, etc., which are predominantly paradirecting catalysts when used as alkylation catalysts may be used for the dealkylation reaction. A most preferred dealkylation catalyst is aluminum chloride.

The amount of catalyst used is an amount sufficient to promote dealkylation of the substituted phenol reactant. While an amount as little as 0.1 mole percent up to amounts of about 20 mole percent based on the weight of the di-substituted phenol reactant can be used, for best results it is desirable to employ an even greater amount of catalyst up to, for example, 120 mole percent.

A variety of well-known hydrolysis procedures can be used for converting the 4-(α-alkyl-α-cyano-methyl)-phenol to the corresponding α-alkyl-4-hydroxyphenylacetic acid. The hydrolysis can be performed in the presence of water and a suitable polar organic solvent such as low-molecular weight alcohols (e.g., methanol or ethanol), 1,4-dioxane, acetone, low-molecular weight carboxylic acids (e.g., acetic acid or propionic acid), N-methylpyrrolidinone, dimethylsulfoxide or the like.

While hydrolysis may be performed in a neutral system or an acidic system, basic hydrolysis is preferred. The reagent of choice is aqueous sodium hydroxide. Reaction temperatures will usually fall between 0° C. and the boiling point of the reaction medium. However, temperatures above the boiling point of the reaction medium can be utilized at elevated pressures to increase the rate of hydrolysis, if desired. These and other details of the hydrolysis reaction can be found in the literature—see, for example, March, *Advanced Organic Chemistry*, (McGraw-Hill, New York, 1977), pp. 809–10 and references cited therein, all disclosures of which are incorporated herein by reference.

The practice of this invention will be still further apparent by the following illustrative examples.

EXAMPLE 1

Preparation of
4-(α-Isopropyl-α-Oxo-Methyl)-2,6-Di-Tertiary-Butyl Phenol

Aluminum chloride (15 g.) was added to 15 ml. of isobutyryl chloride in a 50 ml. round bottom flask with cooling. In a separate vessel, 2,6-di-tertiary-butyl phenol (18.3 g.; 88.63 mmoles) was dissolved in 15 ml. of isobutyryl chloride and the mixture was cooled to −10° C. Both solutions were cooled to −10° C. and rapidly mixed together. A sharp exotherm was noted. After 1 minute, the mixture was poured into ice and the resulting precipitate was isolated by filtration. After recrystallization from hexane, 17.3 g. (70.7% yield) of 4-(α-isopropyl-α-oxo-methyl)2,6-di-tertiary-butyl phenol (characterized by NMR and VPC) was isolated.

EXAMPLE 2

The procedure of Example 1 was repeated three times using twice the amount of reactants each time and the combined product was recrystallized from hexane to yield 96.74 g. (65.9% yield) of the 4-(α-isopropyl-α-oxo-methyl)2,6-di-tertiary-butyl phenol as characterized by NMR and VPC.

EXAMPLE 3

Reduction of
4-(α-Isopropyl-α-Oxo-Methyl)2,6-Di-Tertiary-Butyl Phenol to the Corresponding
4-(α-Isopropyl-α-Hydroxy-Methyl)2,6-Di-Tertiary-Butyl Phenol Lithium aluminum hydride (0.23 g.; 6 mmoles) was added to 10 ml. diethyl ether in a reaction vessel. Into a separate vessel, 4-(α-isopropyl-α-oxo-methyl)2,6-di-tertiary-butyl phenol (2.24 g.; 8 mmoles) was dissolved in 40 ml. diethyl ether and thereafter slowly added to the lithium aluminum hydride mixture with stirring. After complete addition, the mixture was heated at reflux temperature for 1 hour and then cooled to ambient temperature. A sufficient amount of water was added to the resultant reaction mixture to react with the excess hydride followed by the addition of an amount of 10% $H_2SO_4$ sufficient to dissolve aluminum salts formed during the reaction to give a 52.0% yield (VPC) of the corresponding 4-(α-isopropyl-α-hydroxy-methyl)2,6-di-tertiary-butyl phenol.

EXAMPLE 4

Reduction of
4-(α-Isopropyl-α-Oxo-Methyl)2,6-Di-Tertiary-Butyl Phenol to the Corresponding
4-(α-Isopropyl-α-Hydroxy-Methyl)2,6-Di-Tertiary-Butyl Phenol 4-(α-Isopropyl-α-oxo-methyl)2,6-di-tertiary-butyl phenol (1 g.; 3.6 mmoles) was dissolved in 20 ml. ethanol. Sodium borohydride (0.3 g.; 7.8 mmoles) was added to the ketone mixture with stirring at room temperature. The resultant mixture was added to an excess of water containing a small amount of sodium hydroxide and stirred for a few minutes at room temperature until product precipitated from solution which was recovered by filtration, washed with water and dried (MgSO4) to give 0.78 g. (80% yield) of 4-(α-isopropyl-α-hydroxy-methyl)2,6-di-tertiary-butyl phenol as characterized by NMR and VPC.

EXAMPLE 5

Reduction of
4-(α-Isopropyl-α-Oxo-Methyl)2,6-Di-Tertiary-Butyl Phenol to the Corresponding
4-(α-Isopropyl-α-Hydroxy-Methyl)2,6-Di-Tertiary-Butyl Phenol 4-(α-Isopropyl-α-oxo-methyl)2,6-di-tertiary-butyl phenol (20 g., 72.5 mmoles) was dissolved in 350 ml. ethanol in a 500 ml. round bottom flask equipped with a magnetic stirring bar. Powdered sodium borohydride (10. g.) was added incrementally to the reaction mixture over a period of time of ~1.5 hours and the resultant mixture was left at room temperature over the weekend. The solution was added to 1.8 liters of water containing about 20 ml. of 8 N NaOH and stirred at room temperature for 1.5 hours. The solid product was filtered from the solution, washed with water, dried (MgSO4) and recrystallized from hexane with charcoal to give 9.17 g. (45% yield) of 4-(α-isopropyl-α-hydroxy-methyl)2,6-di-tertiary-butyl phenol as characterized by NMR and VPC.

EXAMPLE 6

Reduction of
4-(α-Isopropyl-α-Oxo-Methyl)2,6-Di-Tertiary-Butyl Phenol to the Corresponding
4-(α-Isopropyl-α-Hydroxy-Methyl)2,6-Di-Tertiary-Butyl Phenol 4-(α-Isopropyl-α-oxo-methyl)2,6-di-tertiary-butyl phenol (20 g., 72.5 mmoles) was dissolved in 350 ml. ethanol in a 500 ml. round bottom flask equipped with a magnetic stirring bar. Powdered sodium borohydride (12 g.) was added incrementally to the reaction mixture over a period of time of ~4.5 hours. The resultant reaction mixture was added to 1600 ml. water, stirred at room temperature for ~30 minutes to precipitate product from the solution. The product was then filtered, washed with water and dried (MgSO4) to give 19.7 g. (97.8% yield) of 4-(α-isopropyl-α-hydroxy-methyl)2,6-di-tertiary-butyl phenol.

EXAMPLE 7

Preparation of
4-(α-Isopropyl-α-Cyano-Methyl)2,6-Di-Tertiary-Butyl Phenol from
4-(α-Isopropyl-α-Hydroxy-Methyl)-2,6-Di-Tertiary-Butyl Phenol Sodium cyanide (0.53 g.; 10.8 mmoles) and dimethylformamide (5 ml.) were placed in a round bottom flask equipped with a magnetic stirring bar, reflux condenser, addition funnel and nitrogen sweep. The mixture was heated under nitrogen to 110° C. and the 4-(α-isopropyl-α-hydroxy-methyl)2,6-di-tertiary-butyl phenol (1 g.; 3.6 mmoles) dissolved in 10 ml. dimethylformamide was slowly added to the flask over a period of ~15 minutes with stirring followed by stirring at 110° C. for 1 hour. After cooling the resultant reaction mixture to ambient temperature, several milliliters of water and a small amount of NaOH were added to the mixture. The solvent was removed on a rotary evaporator and the residue was dissolved in ethanol, acidified with 6 N HCl and ice was added to precipitate a viscous product which was crystallized from hexane to give 0.64 g. (62% yield) of a yellow solid product characterized by NMR and VPC as 4-(α-isopropyl-α-cyano-methyl)2,6-di-tertiary-butyl phenol.

EXAMPLE 8

Preparation of
4-(α-Isopropyl-α-Cyano-Methyl)2,6-Di-Tertiary-butyl Phenol from
4-(α-Isopropyl-α-Hydroxy-Methyl)2,6-Di-Tertiary-Butyl Phenol The procedure of Example 7 was repeated except for the following changes. After cooling the resultant reaction mixture to ambient temperature, the solvent was removed on a rotary evaporator, the residue was dissolved in ethanol and ice was slowly added to precipitate a viscous product from the solution. The product was filtered, and dried (MgSO4) to give 1.05 g. (100% yield) of 4-(α-isopropyl-α-hydroxy-methyl)2,6-di-tertiary-butyl phenol identified by VPC.

EXAMPLE 9

Preparation of
4-(α-Isopropyl-α-Cyano-Methyl)2,6-Di-Tertiary-Butyl Phenol from
4-(α-Isopropyl-α-Hydroxy-Methyl)-2,6-Di-Tertiary-Butyl Phenol The procedure of Example 7 was repeated exept for the following changes. After cooling the resultant reaction mixture to ambient temperature, the solvent was removed on a rotary evaporator, water was added to the residue and acidified by 6 N HCl which gave 0.97 g. (94% yield) of 4-(α-isopropyl-α-cyano-methyl)2,6-di-tertiary-butyl phenol as characterized by VPC of an oily product which slowly solidified.

EXAMPLE 10

Preparation of 4-(α-isopropyl-α-cyano-methyl)phenol

A solution of 4-(α-isopropyl-α-cyano-methyl)2,6-ditertiary-butyl phenol (30.37 g.; 106.2 mmoles) and 150 ml. toluene was charged to a reactor equipped with a stirrer, thermometer and reflux condenser. Aluminum chloride (17 g.; 127.5 mmoles) was added to the reactor vessel in 3 or 4 increments was added to the reactor vessel in 3 or 4 increments while vigorous agitation was maintained. An exotherm was observed which raised the reaction temperature by ~20° C. After the aluminum chloride addition was complete, the solution was heated to 95° C. for 5 hours under nitrogen. The reaction mixture was then cooled to ambient temperature, washed twice with water to remove aluminum salts formed during the reaction and the solvent and tertiary-butyl-toluene by-product was removed under reduced pressure to yield 20.1 g. (95.3%) of product determined by VPC (internal standard) as 4-(α-isopropyl-α-cyano-methyl)phenol.

In a manner similar to Example 10 above, a number of experiments were carried out varying the temperature, reaction time, ratio of reactants and catalysts. The results were analyzed by vapor phase chromotography with internal standards and are shown in Table I.

EXAMPLE 37

Preparation of α-Isopropyl-4-Hydroxyphenylacetic Acid 4-(α-isopropyl-α-cyano-methyl)phenol (12.88 g.; 74 mm.) was charged to a 30 ml. stainless steel autoclave along with 17.76 g. NaOH and 120 ml. water. The solution was heated at 130° C. for 6 hours with vigorous stirring while maintaining a pressure of between ~35 and 40 psig. After 6 hours, the reaction vessel was cooled to ambient temperature, the reaction mixture was discharged into a separatory funnel, and the pressure vessel was washed with 30 ml. of water which was added to the reaction mixture. The resultant mixture was washed with methylene chloride to remove residual tert-butyl toluene, cooled to ~10° C. and acidified to a pH between 2 and 3 with concentrated hydrochloric acid. The product was separated by filtration, washed with water and dried under pressure (20 mm. Hg/60° C.) to give 14.29 g. (96.0% yield) of α-isopropyl-4-hydroxyphenylacetic acid as characterized by gas chromatography-mass spectral analysis.

In a manner similar to Example 37 above, a number of experiments were carried out varying the temperature, reaction time, pressure and ratio of reactants. The results were analyzed by HPLC using external standards and are shown in Table II.

TABLE I

Preparation of 4-(α-Isopropyl-α-Cyano-Methyl)Phenol

| Experiment No. | 4-(α-isopropyl-α-cyano-2,6-ditertiary-butyl)phenol (g.) | Catalyst (g.) | Solvent (ml.) | Temp. (°C.) | Time (hr.) | % Yield |
|---|---|---|---|---|---|---|
| 11 | 4.80 | DEAC* - 0.22 | — | 160 | 3 | |
|    |      |              |   | 175 | 2 | 36.3 - External Standard |
| 12 | 4.80 | DEAC - 0.22 | — | 180–185 | 6 | 56.4 - External Standard |
| 13 | 5.92 | DEAC - 0.24 | — | 195–200 | 6 | 82.5 - External Standard |
| 14 | 6.5 | AlCl$_3$ - 0.48 | — | 175–180 | 4 | 64.8 - External Standard |
| 15 | 6.5 | AlCl$_3$ - 0.47 | — | 195–200 | 5 | 67.6 - External Standard |
| 16 | 7.0 | DEAC - 0.20 | — | 195–200 | 5 | 50.4 - External Standard |
| 17 | 6.8 | DEAC - 0.48 | — | 200 | 5 | 55.0 - External Standard |
| 18 | 4.0 | TEA** - 0.29 in toluene | — | 180 | 5 | trace |
| 19 | 4.26 | DEAC - 0.29 | — | 180 | 5 | 63.2 |
| 20 | 3.75 | AlCl$_3$ - 0.30 | — | 180 | 5 | 68.0 |
| 21 | 5.04 | DEAC - 0.30 in phenol | — | 195–200 | 5 | mostly starting material |
| 22 | 7.65 | AlCl$_3$ - 1.50 | — | 170 | 5 | 55.9 |
| 23 | 6.01 | AlCl$_3$ - 0.69 | — | 170 | 5 | 63.8 |
| 24 | 6.01 | AlCl$_3$ - 0.69 | toluene - 4.5 | 140 | 5 | 14.7 |
| 25 | 4.54 | DEAC - 0.20 | — | 170 | 5 | 38.4 |
| 26 | 7.67 | AlCl$_3$ - 0.60 | — | 170–175 | 5 | 45.4 |
| 27 | 6.86 | AlCl$_3$ - 4.00 | toluene - 50 | 80–85 | 5 | 91.2 |
| 28 | 6.86 | AlCl$_3$ - 4.00 | toluene - 50 | 100–105 | 5 | 94.2 |
| 29 | 8.11 | AlCl$_3$ - 4.45 | toluene - 60 | 90 | 5 | 92.3*** |
| 30 | 24 | AlCl$_3$ - 11.40 | toluene - 100 | 95–100 | 4 | 93.8 |
| 31 | 10 | AlCl$_3$ - 5.60 | toluene - 50 | 95 | 5 | 88.1 |
| 32 | 10 | AlCl$_3$ - 5.60 | toluene - 50 + H$_2$O (.03 g.) | 95 | 5 | 81.8 |
| 33 | 8.9 | AlCl$_3$ - 4.96 | toluene - 45 | 90 | 5 | 100 |
| 34 | 9.3 | AlCl$_3$ - 5.20 + CH$_3$NO$_2$**** - 2.38 | toluene - 50 | 90 | 6 | 85.1 |
| 35 | 12.87 | AlCl$_3$ - 7.20 | toluene - 65 | 90–95 | 4 | 90.9 |
| 36 | 28.6 | AlCl$_3$ - 19.34 | toluene - 117 | 95 | 4 | 84.6 |

*DEAC = diethyl aluminum chloride
**triethyl aluminim
***isolated yield
****p-nitromethane

TABLE II

Preparation of α-Isopropyl-4-Hydroxyphenylacetic Acid

| Experiment No. | 4-(α-isopropyl-α-cyano-methyl)-phenol (g.) | Catalyst (g.) | Solvent (ml.) | Temp. (°C.) | Pressure (psig) | Time (hr.) | % Yield |
|---|---|---|---|---|---|---|---|
| 38 | 1.152 | NaOH - 1.39 | $H_2O$ - 10 | reflux | ambient | 17 | 82.3 |
| 39 | 1.29 | NaOH - 1.48 | $H_2O$ - 10 | reflux | ambient | 17 | 100 |
| 40 | 9.77 | NaOH - 13.48 | $H_2O$ - 100 | 130° | 35 | 6 | 85 |
| 41 | 10.89 | NaOH - 15.6 | $H_2O$ - 100 | 130° | 35 | 6 | 86.6 |
| 42 | 14.27 | NaOH - 19.7 | $H_2O$ - 110 | 130° | 35 | 5 | 87.5 |

Having disclosed the process of the present invention, one skilled in the art can readily envision various modifications and changes which are nevertheless within the scope of the invention. Therefore, it is desired that the process of this invention be limited only by the lawful scope of the appended claims.

I claim:

1. A process for the preparation of 4-(α-alkyl-α-cyano-methyl)2,6-di-substituted phenol having the formula

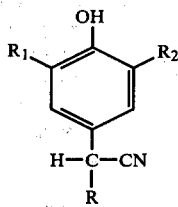

wherein R is methyl, ethyl, n-propyl, or isopropyl and $R_1$ and $R_2$ are the same or different monovalent substituent selected from the group consisting of alkyl, aralkyl and cyclic alkyl radicals which comprises reacting a (i) di-substituted phenol having the formula

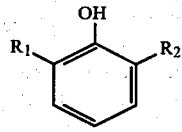

wherein $R_1$ and $R_2$ are as defined above with a Friedel-Crafts addition agent in the presence of a Friedel-Crafts catalyst to form the corresponding 4-(α-alkyl-α-oxo-methyl)2,6-di-substituted phenol, (ii) reducing said 4-(α-alkyl-α-oxo-methyl)2,6-di-substituted phenol thus produced to form the corresponding 4-(α-alkyl-α-hydroxy-methyl)2,6-di-substituted phenol and thereafter (iii) reacting said 4-(α-alkyl-α-hydroxy-methyl)2,6-di-substituted phenol with an alkali metal or an alkali earth metal cyanide in a suitable reaction solvent to form the corresponding 4-(α-alkyl-α-cyano-methyl)2,6-di-substituted phenol.

2. The process of claim 1 wherein $R_1$ and $R_2$ are the same or different monovalent substituent selected from the group consisting of alkyl, aralkyl and cyclic alkyl radicals containing from 1 to about 40 carbon atoms.

3. The process of claim 1 wherein said Friedel-Crafts addition agent is an acyl halide having the formula

wherein R is methyl, ethyl, n-propyl or isopropyl and X is —Cl, —Br, or —I.

4. The process of claim 1 wherein said Friedel-Crafts catalyst is a Lewis acid selected from the group consisting of $AlCl_3$, $AlBr_3$, $FeCl_3$, $PCl_3$, $PCl_5$, $BF_3$, $ZnCl_2$, $TiCl_4$, HF, $H_2SO_4$, $H_3PO_4$, $P_2O_5$, $TeCl_2$ and $SnCl_4$.

5. The process of claim 1 wherein said reduction of (ii) is effected by means of palladium-catalyzed hydrogenation.

6. The process of claim 1 wherein said reduction of (ii) is effected by means of a metal hydride.

7. The process of claim 6 wherein said metal hydride is selected from the group consisting of lithium aluminum hydride, lithium borohydride and sodium borohydride.

8. The process of claim 1 wherein the alkali metal cyanide is sodium cyanide.

9. The process of claim 1 wherein the solvent is a dipolar aprotic solvent.

10. The process of claim 9 wherein the solvent is selected from the group consisting of dimethyl sulfoxide, N,N-dimethylformamide, N,N-dimethylacetamide, dimethyl sulfone, tetramethylene sulfone, N-methylpyrrolidinone and acetonitrile.

11. The process of claim 1 wherein the reaction of (iii) with an alkali metal or an alkaline earth metal cyanide is carried out at an elevated temperature.

12. The process of claim 11 wherein said reaction is carried out at a temperature of at least 50° C.

13. A process for preparing α-alkyl-4-hydroxyphenylacetic acid having the formula

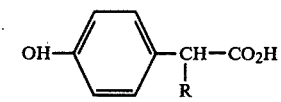

wherein R is methyl, ethyl, n-propyl or isopropyl which comprises (i) preparing a 4-(α-alkyl-α-cyano-methyl)2,6-di-substituted phenol having the formula

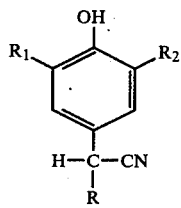

wherein R is as defined above and $R_1$ and $R_2$ are the same or different monovalent substituent selected from the group consisting of alkyl, aralkyl and cyclic alkyl radicals by reacting a di-substituted phenol having the formula

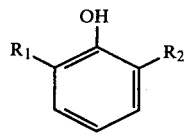

wherein $R_1$ and $R_2$ are as defined above with a Friedel-Crafts addition agent in the presence of a Friedel-Crafts catalyst to form the corresponding 4-(α-alkyl-α-oxo-methyl)2,6-di-substituted phenol, (ii) reducing the 4-(α-alkyl-α-oxo-methyl)2,6-di-substituted phenol thus produced to form the corresponding 4-(α-alkyl-α-hydroxy-methyl)2,6-di-substituted phenol, (iii) reacting said 4-(α-alkyl-α-hydroxy-methyl)2,6-di-substituted phenol with an alkali metal or an alkaline earth metal cyanide in a suitable solvent to form the corresponding 4-(α-alkyl-α-cyano-methyl)2,6-di-substituted phenol, (iv) dealkylating the substituent groups ortho to the hydroxyl group from said 4-(α-alkyl-α-cyano-methyl)2,6-di-substituted phenol to form the corresponding 4-(α-alkyl-α-cyano-methyl)phenol and (v) converting said 4-(α-alkyl-α-cyano-methyl)phenol by hydrolysis to the corresponding α-alkyl-4-hydroxyphenylacetic acid.

14. The process of claim 13 wherein $R_1$ and $R_2$ are the same or different monovalent substituent selected from the group consisting of alkyl, aralkyl and cyclic alkyl radicals containing from 1 to about 40 carbon atoms.

15. The process of claim 13 wherein said Friedel-Crafts addition agent is an acyl halide having the formula

wherein R is methyl, ethyl, n-propyl or isopropyl and X is —Cl, —Br, or —I.

16. The process of claim 13 wherein said Friedel-Crafts catalyst is a Lewis acid selected from the group consisting of $AlCl_3$, $AlBr_3$, $FeCl_3$, $PCl_3$, $PCl_5$, $BF_3$, $ZnCl_2$, $TiCl_4$, HF, $H_2SO_4$, $H_3PO_4$, $P_2O_5$, $TeCl_2$ and $SnCl_4$.

17. The process of claim 13 wherein said reduction of (ii) is effected by means of paladium-catalyzed hydrogenation.

18. The process of claim 13 wherein said reduction of (ii) is effected by means of a metal hydride.

19. The process of claim 18 wherein said metal hydride is selected from the group consisting of lithium aluminum hydride, lithium borohydride and sodium borohydride.

20. The process of claim 13 wherein the alkali metal cyanide is sodium cyanide.

21. The process of claim 13 wherein the solvent is a dipolar aprotic solvent.

22. The process of claim 21 wherein the solvent is selected from the group cosisting of dimethyl sulfoxide, N,N-dimethylformamide, N,N-dimethylacetamide, dimethyl sulfone, tetramethylene sulfone, N-methylpyrrolidinone and acetonitrile.

23. The process of claim 13 wherein the reaction of (iii) with an alkali metal or an alkaline earth metal cyanide is carried out at an elevated temperature.

24. The process of claim 23 wherein said reaction is carried out at least 50° C.

25. The process of claim 13 wherein dealkylation is effected by heating said 4-(α-alkyl-α-cyano-methyl)2,6-di-substituted phenol at an elevated temperature in the presence of a dealkylation catalyst and an aromatic hydrocarbon.

26. The process of claim 13 wherein said dealkylation is carried out at a temperature of from about 60° C. to about 250° C.

27. The process of claim 13 wherein said dealkylation catalyst is selected from a phenoxy derivative of aluminum, magnesium, iron, zinc, phosphorus, zirconium, titanium, bismuth or tin.

28. The process of claim 13 wherein said aromatic hydrocarbon is selected from the group consisting of benzene, toluene, ethylbenzene, xylene, trimethyl benzene, tetrahydronaphthylene, isobutylbenzene, phenol, cresol, o-isopropylphenol, 4-hydroxyanisole, halobenzenes and aromatic ethers.

29. The process of claim 13 wherein dealkylation is carried out under an inert, nonreactive atmosphere.

30. The process of claim 13 wherein said hydrolysis is carried out in a basic medium.

31. The process of claim 13 wherein said hydrolysis is carried out in the presence of aqueous sodium hydroxide.

* * * * *